United States Patent
Baum et al.

(10) Patent No.: US 6,743,626 B2
(45) Date of Patent: Jun. 1, 2004

(54) ARTIFICIAL SALIVARY GLAND

(75) Inventors: Bruce J. Baum, Bethesda, MD (US); Kenneth M. Yamada, Bethesda, MD (US); Edna Cukierman, Rockville, MD (US); David Mooney, Ann Arbor, MI (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/938,706

(22) Filed: Aug. 23, 2001

(65) Prior Publication Data

US 2003/0031696 A1 Feb. 13, 2003

Related U.S. Application Data (63) Continuation of application No. PCT/US00/04489, filed on Feb. 23, 2000.
(60) Provisional application No. 60/121,335, filed on Feb. 24, 1999.

(51) Int. Cl.[7] .......................... C12N 15/85; C12N 15/86
(52) U.S. Cl. ..................................................... 435/325
(58) Field of Search ................. 435/325, 1.1; 514/2.21; 424/93.1, 93.2, 93.6

(56) References Cited

U.S. PATENT DOCUMENTS

| 4,745,101 A | 5/1988 | Aonuma |
| 5,462,870 A | 10/1995 | Chopra |
| 5,741,671 A | 4/1998 | Agre |

FOREIGN PATENT DOCUMENTS

| WO | WO 9745533 | 12/1997 |
| WO | WO 9901538 | 1/1999 |

OTHER PUBLICATIONS

Anderson, W. French, Human gene therapy, Apr. 1998, Nature, 391 (Supp): 25–30.*
Kmiec, Eric B., Gene Therapy, May 1999, American Scientist, 87: 240–247.*
Verma, Inder M., Gene therapy—promises, problems and prospects, Sep. 1997, Nature, 389: 239–242.*
Aframian et al. Tissue Compatibility of Two Biodegradable Tubular Scaffolds Implanted Adjacent to Skin or Buccal Mucosa in Mice, 2002, Tissue Engineering, 8(4): 649–659.*
Adesanya, M. R., et al. (1996) Immediate Inflammatory Responses to Adenovirus–Mediated Gene Transfer in Rat Salivary Glands. Hum. Gene Ther. 7:1085–1093.
Baum, B. J. (1993) Principles of Saliva Secretion, Ann. N. Y. Acad. Sci. 694:17–23.
Baum, B. J., et al. (1990) Dispersed Salivary Acinar Cell Preparations for Use in Studies of Neuroreceptor–Coupled Secretory Events. Methods Enzymol. 192:26–37.
Baum, B. J., et al. (1999) Re–engineering the Functions of a Terminally Differentiated Epithelial Cell In Vivo. Ann. N.Y. Acad. Sci. 875:294–300.
Bramson, J. L., et al. (1995) The use of adenoviral vectors for gene therapy gene transfer in vivo. Curr. Opin. Biotechnol. 6:590–595.
Cook, D. I., et al. (1994) Secretion by the Major Salivary Glands. In Physiology of the Gastrointestinal Tract 1061–1117.

(List continued on next page.)

*Primary Examiner*—James Ketter
*Assistant Examiner*—Ramin Akhaven
(74) *Attorney, Agent, or Firm*—Knobbe, Martens, Olson & Bear LLP (57) ABSTRACT

The present invention generally relates to the field of oral prosthetics and tissue engineering. More specifically, a novel, artificial fluid secreting prosthesis for non-invasive insertion is disclosed. Further, methods of use of the foregoing are provided.

1 Claim, 2 Drawing Sheets

OTHER PUBLICATIONS

Delporte, C., et al. (1997) Relationship between the Cellular Distribution of the $\alpha_v\beta_{3/5}$ Integrins and Adenoviral Infection in Salivary Glands. Lab. Invest 77(2):167–173.

Delporte, C., et al. (1998) Relationship between Adenovirus–Mediated Aquaporin 1 Expression and Fluid Movement across Epitheliel Cells. Biochem. Biophys. Res. Commun. 246:584–588.

Delporte, C., et al. (1997) Increased fluid secretion after adenoviral–mediated transfer of the aquaporin–1 cDNA to irradiated rat salivary glands. PNAS USA 94:3268–3273.

Eid, A., et al. (1997) Salivary Gland Transplantation: A Canine Model. Transplantation 64(5):679–683.

Goldfine, I. D., et al. (1997) The endocrine secretion of human insulin and growth hormone by exocrine glands of the gastrointestinal tract. Nature Biotechnol. 15:1378–1382.

He, X., et al. (1998) Systemic action of human growth hormone following adenovirus–mediated gene transfer to rat submandibular glands. Gene Ther. 5:537–541.

Hoffman, M. P., et al. (1996) Role of laminin–1 and TGF–β3 in acinar differentiation of a human submandibular gland cell line (HSG). J. Cell Sci. 109:2013–2021.

Kagami, H., et al. (1996) Evidence for the Systemic Delivery of a Transgene Product from Salivary Glands. Hum. Gene Ther. 7:2177–2184.

Kagami, H., et al. (1998) Repetitive Adenovirus Administration to the Parotid Gland: Role of Immunological Barriers and Induction of Oral Tolerance. Hum. Gene Ther. 9:305–313.

Kashima, H. K., et al. (1965) Postirradiation Sialadenitis. Am. J. Roentgenol. Radium Ther. Nucl. Med. 94(2):271–291.

Kozarsky, K. F. & Wilson, J. M. (1993) Gene therapy: adenovirus vectors. Curr. Opin. Genetics Develop. 3:499–503.

Lafrenie, R. M., et al. (1998) Adhesion to Fibronectin or Collagen I Gel Induces Rapid, Extensive, Biosynthetic Alterations in Epithelial Cells. J. Cell, Physiol. 175:163–173.

Langer, R. and Vacanti, J. P. (1993) Tissue Engineering. Science 260:920–926.

Lawrence, A. M., et al. (1976) Salivary Gland Hyperglycemic Factor: An Extrapancreatic Source of Glucagon–Like Material. Science 195:70–72.

Mandel, I.D. (1989) The role of saliva in maintaining oral homeostasis. J. Am. Dent. Assoc. 119:298–304.

Mastrangeli, A. et al. (1994) Direct in vivo adenovirus–mediated gene transfer to salivary glands. Am. J. Physiol. 266:G1146–G1155.

Mooney, D. J. & Rowly, J. A. (1997) Tissue Engineering; Integrating Cells and Materials To Create Functional Tissue Replacements. In Controlled Drug Delivery 333–346.

Mooney, D. J., et al. (1994) Design and Fabrication of Biodegradable Polymer Devices to Engineer Tubular Tissues. Cell Transplant. 3(2):203–210.

Preston, G. M. & Agre, P. (1991) Isolation of the cDNA for erythrocyte integral membrane protein of 28 kilodaltons: Member of an ancient channel family. PNAS USA 88:11110–11114.

Royce, L. S., et al. (1991) Differentiation of a Salivary Duct Cell Line on a Reconstituted Basement Membrane. J. Dental Research vol. 70, Special Issue Apr., p. 449.

Royce, L. S., et al. (1993) Human neoplastic submandibular intercalated duct cells express an acinar phenotype when cultured on a basement membrane matrix. Differentiation 52:247–255.

Shirasuna, K., et al. (1981) A Neoplastic Epithelial Duct Cell Line Established from an Irradiated Human Salivary Gland. Cancer 48:745–752.

Silverman, S. Jr. (1992) Precancerous Lesions and Oral Cancer in the Elderly. Clin. Geriatic Med. 8:529–541.

Tieche, J. M., et al (1980) Isolation and Partial Characterization of a Porcine Parotid Hormone that Stimulates Dentinal Fluid Transport. Endocrinology 106(6):1994–2005.

Young, J. A. and van Lennep, E. W. (1979) Transport in Salivary and Salt Glands. In Membrane Transport in Biology 4:563–674.

Zheng, C., et al. (1998) Growth Factor Regulation of the Amylase Promoter in a Differentiating Salivary Acinar Cell Line. J. Cell. Physiol. 177:628–635.

Baum, B. J. (Jun. 27, 1998) Lecture, Nagoya, Japan and (Jul. 20, 1998) Lecture Banff, Canada (3 Figures).

* cited by examiner

ARTIFICIAL SALIVARY GLAND

CROSS-REFERENCE TO RELATED APPLICATIONS

This application is a continuation of International Application number PCT/US00/04489 and claims the benefit of priority of International Application No. PCT/US00/04489 having international filing date Feb. 23, 2000, designating the United States of America and published in English, which claims the benefit of priority of U.S. application Ser. No. 60/121,335, filed Feb. 24, 1999; both of which are hereby expressly incorporated by reference in their entireties.

FIELD OF THE INVENTION

The present invention generally relates to the field of oral prosthetics and tissue engineering. More specifically, a novel, artificial fluid secreting prosthesis for non-invasive insertion is disclosed. Further, methods of use of the foregoing are provided.

BACKGROUND OF THE INVENTION

For many years, investigators have studied diseases of the mouth and mechanisms by which salivary glands produce their secretions. (Bricker et al., eds., "Oral Diagnosis, Oral Medicine and Treatment Planning," Lea & Febiger, Philadelphia, Pa., 1994; Baum et al., *Methods Enzymol*, 192:26–37 (1990); and Baum et al., *Ann. NY Acad. Sci*, 694:17–23 (1993)). Salivary glands have provided a valuable experimental model for generations of scientists interested in neurofunctional controls, from Claude Bernard and Ivan Pavlov to the present day. They are highly responsive epithelial tissues whose function can be readily and non-invasively measured. (Young et al., "Secretion of salivary and salt glands," *Membrane Transport in Biology*, Vol 4, Giebisch et al., eds., Springer-Verlag, Berlin/New York, 1979:563–674; and Mandel, *J. Amer. Dent. Assoc.*, 119:298–304 (1989)).

All salivary glands are compound tubuloalveolar glands. Small intrinsic salivary glands are scattered within the mucosa of the tongue, palate, lips, and cheeks. Saliva from these glands keeps the mouth moist at all times. Large extrinsic salivary glands secrete saliva during eating. In humans there are three extrinsic salivary glands (parotid, submandibular, and sublingual) that lie external to the mouth but are connected to the mouth through ducts. From an open mouth, the cannulation of the duct orifice, a procedure that in humans requires no anesthesia, affords direct access to the luminal membrane of virtually every cell in this secretory tissue.

Salivary glands consist almost entirely of well-differentiated epithelial cells that exist as a monolayer bordering on an extensively arborized lumen. (Cook et al., "Secretion by the major salivary glands," *Physiology of the Gastrointestinal Tract*, Johnson, ed., Raven, New York, 1994:1061–1117). The secretory cells of these glands produce a watery secretion composed of enzymes and ions, while mucous cells produce mucous. Depending on the type of salivary gland, different amounts of secretory cells and mucous cells are present There are many subjects who effectively have lost all functional salivary epithelium, both acinar and ductal, and experience severe salivary hypofunction. Each year in the United States alone, approximately 30,000 individuals undergo therapeutic ionizing radiation (IR) for head and neck malignancies. (Silverman, *Clin. Geriatric Med.*, 8:529–541 (1992)). Acinar cells—the fluid, salt, and protein-secretory cell type in the glands—are very sensitive to radiation and are readily destroyed during radiation therapy. (Kashima et al., *Am. J. Roentgenol Radium Ther. Nucl. Med.*, 94:271–291 (1965)). In addition to irradiated subjects, many other individuals with Primary Sjogren's syndrome or an autoimmune exocrinopathy also exhibit salivary gland hypofunction. In consequence, individuals having hypofunctional salivary glands suffer from rampant dental caries (decay), frequent mucosal infections (such as oral Candidiasis), dysphagia (swallowing difficulties), as well as, considerable pain and discomfort.

At present, there is no conventional effective treatment of salivary gland hypofunction. While gene transfer to glandular epithelial tissue offers promise, at present, the expression of transferred genes is transient at best and many subjects lack glandular epithelial tissue for gene transfer altogether. The transplantation of mammalian salivary glands has also been tried but this option is clinically undesirable because of an insufficient donor supply, the continuous need for immunosuppression, and surgical difficulty. (Eid et al., *Transplantation*, 64:679–683 (1997)). In view of the foregoing, and not withstanding the various efforts exemplified in the prior art, there remains a need for an artificial fluid secreting prosthesis and a deployment methodology for oral implantation so as to treat individuals suffering from salivary gland hypofunction.

BRIEF SUMMARY OF THE INVENTION

Compositions and methods based on the discovery of an artificial fluid secreting prosthesis are disclosed. In a first set of experiments, it is demonstrated that subjects having irradiated salivary gland cells can be induced to secrete fluid subsequent to transfer of a gene encoding aquaporin-1 (AQP1). In a second set of experiments, it is shown that heterologous genes transferred to salivary gland cells, such as human α1-antitrypsin (hα1AT) and human growth hormone (hGH), can be expressed in vivo and these products are detected in the blood of the recipient organism. In a third set of experiments, an artificial salivary gland is constructed. This device has a support, an attachment surface joined to the support, and joined to the attachment surface are a polarized monolayer of allogenic or autologous cells that are engineered to secrete ions and water unidirectionally.

DETAILED DESCRIPTION OF THE INVENTION

An orally-implantable, artificial fluid-secreting prosthesis, also termed "artificial salivary gland", and methods of use of the foregoing have been discovered. The disclosure that follows stems from the results from three distinct areas of tissue engineering: (i) the in vivo repair of salivary glands considered to be irreversibly damaged due to irradiation; (ii) the in vivo redesign of salivary glands to function in an endocrine capacity; and (iii) the replacement of destroyed glands with an artificial salivary gland. Studies directed at the replacement of destroyed salivary gland tissue particularly focus on the creation of a functional new tissue using allogenic or autologous cells grown and appropriately organized on a suitable biocompatible support.

Approaches of in vivo re-engineering of salivary epithelial cells (e.g., for repair or redesign of function) have utilized replication-deficient recombinant adenoviruses to transfer genes into the target cells. After introduction of recombinant adenoviruses to the glands via intraductal delivery through the excretory duct orifice, these vectors readily infect both ductal and acinar cells in rodent glands, typically resulting in ~20–30% of the cells transduced. (Mastrangeli et al., *Am. J. Physiol.*, 266:G1146–G1155 (1994) and Delporte et al., *Lab Invest.*, 77:167–173 (1997)). While adenoviral vectors are extremely efficient at transferring genes to, and thus changing the phenotype of, a salivary cell in vivo, they are not without negative features. The two most significant drawbacks of recombinant adenoviral vectors are their inability to integrate their DNA into the host cell chromosome and the induction of a potent immune response involving innate, cellular and humoral immunity. (Kozarsky et al., *Curr. Opin. Genetics Develop.*, 3:499–503 (1993); and Bramson et al., *Curr. Opin. Biotechnol*, 6:590–595 (1995)). As in other parenchymal tissues, the consequence of these drawbacks in salivary glands is the transient expression of the transgene. (Adesanya et al., *Hum. Gene Ther.*, 7:1085–1093 (1996) and Kagami et al., *Hum. Gene Ther.*, 9:305–313 (1998)). Nonetheless, recombinant adenoviral vectors were extremely useful for proof of the following principle experiments. Other vectors used to express transgenes in the engineered cells of the invention include adenoassociated virus and a hybrid adenoretrovirus. Cationic liposomes are also used to transfer trangenes to salivary cells so as to construct some of the embodiments of the invention. The discussion below details several studies on in vivo salivary gland repair.

In vivo Salivary Gland Repair

Initially, a way to convert the irradiation-surviving absorptive ductal epithelial cells into a secretory, water-permeable phenotype was investigated. The remaining ductal epithelial cells were thought to be capable of generating a $KHCO_3$ rich fluid, in the absence of acinar cells, if they could be transduced with (and expressed) a gene encoding a facilitated water permeability pathway, a water channel. AQP1 is the archetypal mammalian water channel protein and generally exists in a non-polarized distribution about the plasma membrane. (Preston and Agre, *Proc. Natl. Acad. Sci USA*, 88:11110–11114 (1991)). A recombinant, type 5 adenovirus encoding aquaporin-1 (AQP1) was constructed and the ability of a recombinant virus, termed "AdhAQP1", to enhance fluid secretion from rat submandibular glands that had been exposed 4 months earlier to 21 Gy X-irradiation was analyzed. (See Table 1). (See also Delporte et al., *Proc. Natl. Acad. Sci. USA*, 94:3268–3273 (1997) and (Delporte et al., *Biochem. Biophys. Res. Commun.*, 246:584–588 (1998), herein incorporated by reference).

TABLE 1

Effect of AdhAQPI on Fluid Secretion from Irradiated Rat Submandibular Glands*

| Treatment | Saliva Flow ($\mu$l/100 g body weight in 15 min) ± SEM |
|---|---|
| Sham IR + AddI3I2 | 36.6 ± 6.8 (4) |
| IR + Add1312 | 12.2 ± 3.7 (6) |
| IR + AdhAQP1 | 30.6 ± 3.5 (9) |

*IR = 21 Gy irradiation.
AddI312 is a control virus encoding no transgene while AdhAQPI encodes human AQP1.
Numbers in parentheses refers to the number of animals studied.
Irradiation (or sham treatment) was performed and 4 months later the indicated virus was administered to the submandibular glands. Saliva was collected 3 days later.

Animals receiving a control virus showed ~65% reduction in salivary flow rates when compared to animals that had been sham-irradiated. Animals receiving AdhAQP1, however, secreted saliva at control levels after irradiation. Furthermore, the saliva secreted was significantly higher in $[K^+]$ than control saliva, consistent with a secretory mechanism.

These results encouraged a similar approach for the effective clinical treatment of subjects with radiation-induced salivary hypofunction. The data provided for the possible re-engineering of a cellular phenotype in vivo from a non-fluid secreting to a fluid secreting phenotype. Other experiments demonstrated that near maximal, osmotically-obligated transepithelial water movement can be realized at low levels of cellular transduction, at least in an in vitro model system. The section below describes experiments that demonstrate that salivary glands are useful for the therapeutic delivery of transgene products.

Salivary glands are a useful for the therapeutic delivery of transgene products

There have been several reports that salivary glands are capable of secreting in an endocrine (directly to the bloodstream) as well as exocrine (saliva to the mouth) manner. (See e.g., Lawrence et al., *Science*, 195:70–72 (1977); (Kagami et al., *Hum. Gene Ther.*, 7:2177–2184 (1996)); and Tieche et al., *Endocrinology*, 106:1994–2004 (1980)). Experiments were performed to directly test the ability of rat salivary glands to secrete a foreign transgene product, human α1-antitrypsin (hα1AT), into the bloodstream. A recombinant adenovirus, AdMLPhα1AT, was administered to adult rats and hα1AT levels in serum, saliva, and gland extracts was measured. Hα1AT was detected in all compartments for 4–7 days. Significantly, on day 4, peak levels achieved were ~5 ng/ml (serum), ~70 ng/ml (saliva), and ~10 ng/mg protein (gland extract). Additionally, the concentration of hα1AT in venous blood exiting the gland was consistently higher than that in arterial blood entering the gland. (See Table 2).

TABLE 2

Levels of hα1AT in serum from rat submandibular gland arterial and venous blood after administration of AdMLPhα1AT*

| Sample | hα1AT AT (ng//ml) |
|---|---|
| Carotid Artery | 19.4 ± 10.6 |
| Submandibular Vein | 67.9 ± 27.2 |

*These experiments represent results (mean ± SEM) obtained with 7 animals whose right carotid arteries and submandibular veins were sampled 24 hrs after administration of AdMLPhα1AT ($5 \times 10^9$ pfu) to the right submandibular gland. The range of hα1AT levels in sera from carotid arteries was 0–70.7 ng/ml, while for sera from submandibular veins the levels were 5.5–223.4 ng/ml. In each of the 7 animals, the venous level of hα1AT was greater than the arterial level.

While these studies unequivocally demonstrated that hα1AT could be secreted in an endocrine manner from rat salivary glands, they did not demonstrate that the transgene product secreted from the glands was systemically functional. In subsequent studies, however, it was shown that a different recombinant virus, AdCMVhGH, encoding human growth hormone (hGH) can be used, as well. (See also He et al., *Gene Ther.*, 5:537–541 (1998), herein incorporated by reference). Effective therapeutic levels of hGH, in this case, was ~5 ng/ml in serum, which is comparable to what was achieved with hα1AT. Importantly, hGH can bind to, and activate, rodent GH receptors. Forty-eight hours after intraductal administration of AdCMVhGH to rat submandibular glands, serum hGH levels were ~16 ng/ml versus background levels of ~1 ng/ml seen in control rats. Further, a concomitant increase in serum insulin-like growth factor levels (~33%), serum triglycerides (~2-fold), and the serum BUN/creatinine ratio (~35%) was observed, thus, indicating that the hGH secreted from the salivary glands was physiologically functional and systemically active. In support of these results are recent studies, which demonstrated that measurable levels of endocrine hormones in rat serum could be obtained after the retrograde installation of plasmid DNA into salivary glands. (See e.g., Goldfine et al., *Nature Biotechnol.*, 15:1378–1382 (1997)). In aggregate, the results above demonstrate that salivary glands are a useful target for the therapeutic delivery of transgene products for systemic use. Embodiments of an orally implantable, artificial fluid secreting device for the treatment of salivary gland hypofunction and drug delivery are described in the following section.

Figure 1:
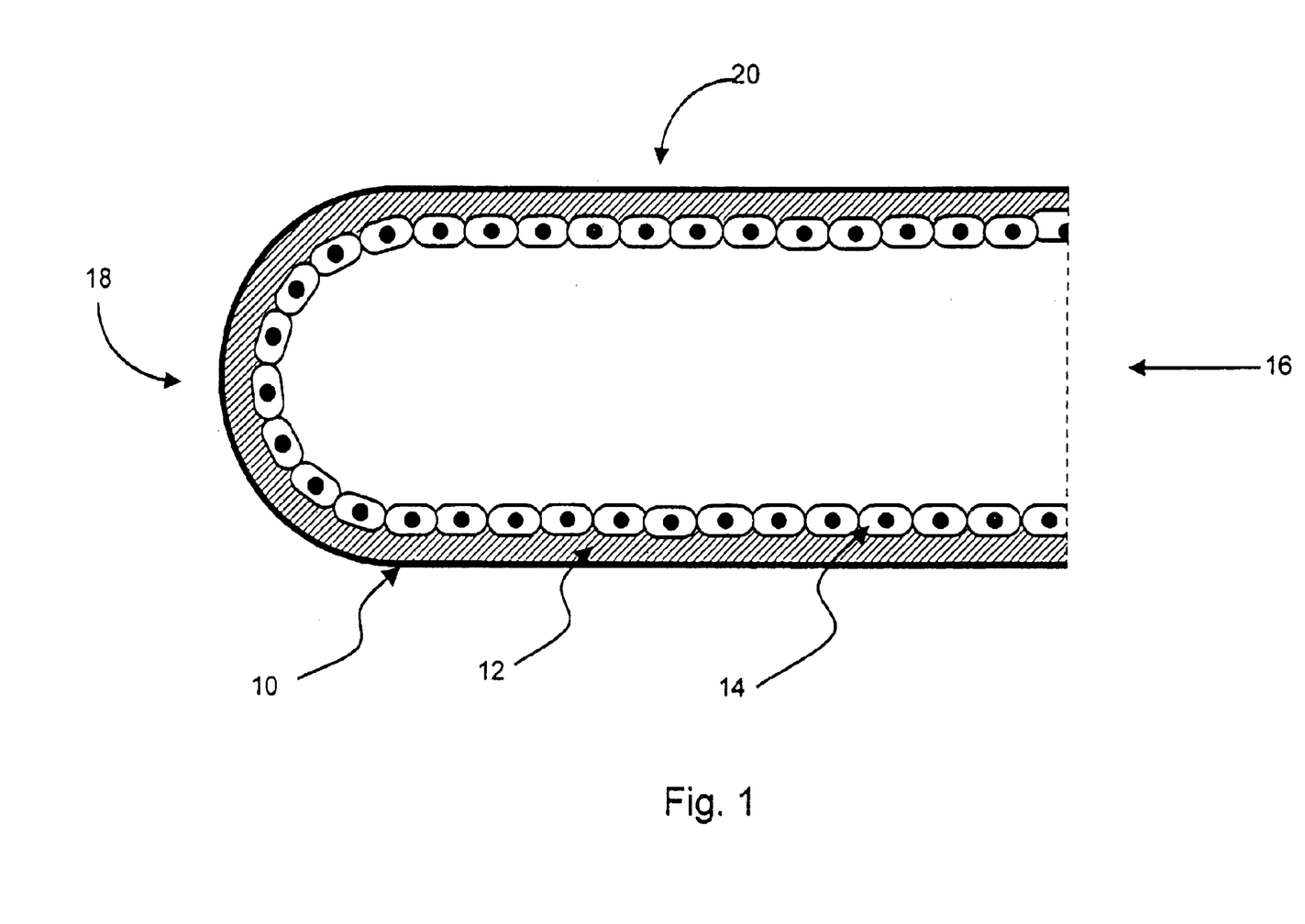
FIG. 1 illustrates one embodiment of an artificial salivary gland constructed as a blind-end tube having • a porous, biodegradable support; • a matrix component (peptides or macromolecules) that promotes formation of a polarized cell monolayer; • allogenic or autologous cells genetically engineered to secrete water and salt unidirectionally; and • an overall form that is easily implantable with an "exit" to the oral cavity.
Figure 2:
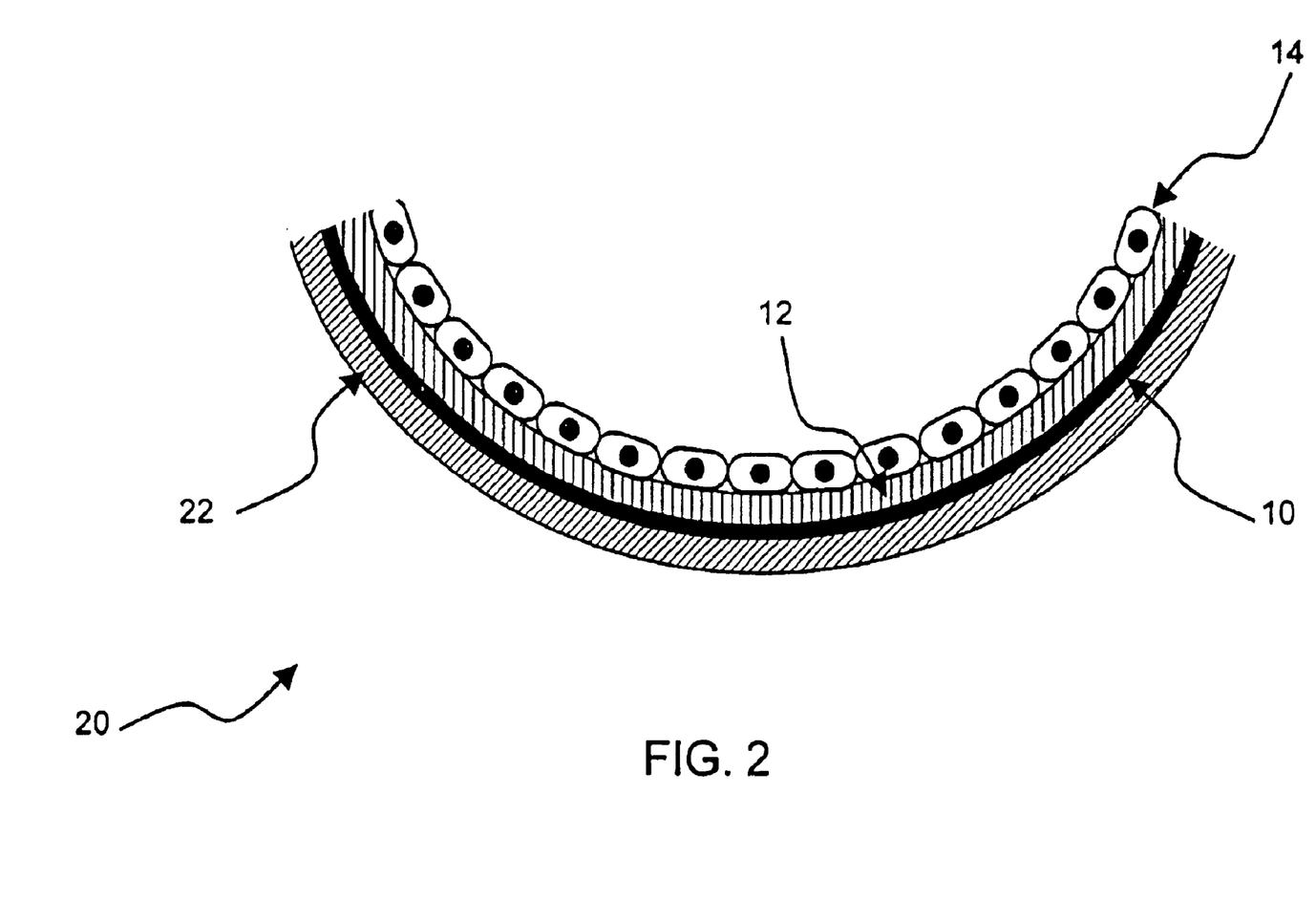
FIG. 2 illustrates another embodiment of the artificial salivary gland having • an attachment surface; • a porous, biodegradable support; • a matrix component (peptides or macromolecules) that promotes formation of a polarized cell monolayer; • allogenic or autologous cells genetically engineered to secrete water and salt unidirectionally; and • an overall form that is easily implantable with an "exit" to the oral cavity.

Embodiments of the Artificial Salivary Gland Can Have a Plurality of Shapes, Sizes, and Degrees of Flexibility With reference to FIGS. 1 and 2, an implantable artificial fluid secreting prosthesis (an "artificial salivary gland") 20 is provided comprising a support 10 having a surface 12 that allows for the attachment of cells 14, which secrete salivary fluids and/or therapeutic agents. In preferred aspects of this embodiment, the artificial fluid secreting prosthesis 20 comprises an oblong, cylindrical, or elliptical shape and has an open proximal end 16 and a closed distal end 18. As used herein, the term "distal" refers to a location closer to the throat and "proximal" refers to a location closer to the mouth. In another embodiment, the proximal end 16 is more narrow than the distal end 18 so as to more appropriately fit the anatomy of some subjects. In other embodiments, the artificial fluid secreting device 20 is a cylindrical or elliptical shape, wherein the proximal end 16 and the distal end 18 are roughly the same shape and size. The artificial salivary gland 20 shown in FIGS. 1 and 2 can also have a support 10 that has an attachment surface 22, which promotes stability of the device 20, tissue ingrowth, and vascularization.

Additional embodiments include a convex shaped prosthesis 20, a concave-shaped prosthesis 20, and a flat, disk-shaped device 20. In contrast to the inwardly disposed cells 14, shown in FIG. 1, additional embodiments have cells 14 that are outwardly disposed on an exterior surface 12, which covers the support 10. (See FIG. 2). The portion of the support not covered with cells 14 also has an attachment surface 22, which promotes stability, tissue ingrowth, and vascularization after implantation. Irregularly shaped embodiments 20 that closely resemble the anatomy of salivary glands are also embodiments and the cells 14 on these devices can be more or less inwardly disposed depending on the structural characteristics of the particular design.

Depending on the subject's anatomy, the type of salivary gland to be replaced, and the extent of salivary gland hypofunction, devices having varied sizes and shapes are implanted taking care not to disrupt any residual salivary gland function. Using techniques known in the art, medical personnel can access the extent to which the epithelial cells of a subject are intact and can take account for the subject's specific anatomical features when selecting specific shapes and designs of the artificial salivary glands 20 to be implanted.

Suitable artificial fluid secreting devices 20 comprise a flexible body that can have an axial length from 1.0 cm to 6.0 cm, a width of 0.2 cm to 4.0 cm, and a thickness of 1.0 mm to 10.0 mm. Many artificial fluid secreting devices 20 have a length within the range of 1.5 cm to 4.0 cm, a width within the range of 0.75 cm to 2.5 cm, and a thickness within the range of 1.5 mm to 7.0 mm. In one embodiment, the artificial fluid secreting device 20 has a length of 2.0 cm to 3.0 cm, a width of 1.5 cm, and a thickness of 2.0 mm to 5.0 mm. The cross sectional area of the device 20 can also vary at different regions of the same device depending on whether a cross-section is taken at the proximal end 16 or distal end 18 and the overall body shape of the device 20. As mentioned above, optimal dimensions can be subject specific, gland specific, and can be determined through routine experimentation by one of skill in the art in view of the disclosure herein.

Due to the irregular cross-sectional configuration of many salivary glands, the cross-sectional configuration of the artificial fluid secreting device 20 can take on any of a wide variety of shapes including, but not limited to, those specific embodiments disclosed herein. In general, the desired shape and size of the artificial fluid secreting device 20 will depend on the shape of the salivary gland orifice and the extent of salivary gland dysfunction. Artificial fluid secreting devices 20 produced in accordance with the teachings herein can be rated according to their secreting area, which represents the total cross-sectional area the device will occupy within a particular salivary gland orifice. In this manner, kits comprising artificial fluid secreting devices 20 of varying sizes and shapes can be manufactured and sold. Such kits would allow for the rapid implantation of an artificial fluid secreting device 20 after a clinician has assessed the shape and size of the salivary duct orifice and any anatomical features that might dictate a specific size and shape of the artificial fluid secreting device 20 to be implanted.

Several embodiments of the artificial fluid secreting device 20 also have a flexible, soft, and pliable structure. The flexibility of the artificial fluid secreting device 20 desirably accommodates natural movement (e.g., movement during eating and drinking) as well as any residual native salivary gland function without compromising the attachment of the artificial fluid secreting device 20. Embodiments having a soft and flexible body minimize the risk of trauma to adjacent tissue. By "flexible", it is intended that artificial fluid secreting device 20 has a support 10 that is amply pliable so that it does not create enough pressure to cause necrosis, atrophy, or erosion. Many more aspects of the support are provided in the specification below.

Embodiments of the Artificial Salivary Gland Can Have Various Supports

By "support" is meant a substratum, a carrier, a resin or any macromolecular structure used to attach or immobilize a cell. A support 10 can be biodegradable or impervious to degradation in the body. Since native salivary epithelia exist essentially as a monolayer lining a lumen, the support 10 preferably induces the polarized cells to form a monolayer affording complete coverage of its surface. Further, a support 10 is preferably porous so as to allow for the flow of water and ions to and from the cells 14 attached to the support 10 and the underlying tissue. In this manner, the artificial salivary gland 20 functions as an ion and fluid pump and remains functionally associated with the underlying tissue in the salivary gland orifice.

The support 10 can have a hydrophobic surface 12 that interacts with the hydrophobic regions of the cell membrane by an hydrophobic non-covalent interaction and, thus, allows the cells 14 to strongly adhere to the support. In this regard, the hydrophobic surface 12 of the support 10 can be a polymer such as plastic or another polymer in which hydrophobic groups have been linked such as polystyrene, polyethylene or polyvinyl. Further, the support 10 can comprise an inorganic carrier such as silicon oxide material (e.g. silica gel, zeolite, diatomaceous earth or aminated glass).

Alternatively, carriers 12 including proteins and oligolpolysaccharides (e.g. cellulose, starch, glycogen, chitosane or aminated sepharose) can be used as a support 10 or in conjunction with another material to make a support 10. In a preferred embodiment, a support 10 is coated with an extracellular matrix protein such as, Matrigel, Vitrogen, fibronectin, laminin, collagen I, collagen IV or another protein such as, gelatin or poly-lysine so as to provide a water and ion permeable surface 12 for the cells 14 to attach and form a polarized monolayer. Still further, a feeder cell layer is used in some embodiments to provide a water and ion permeable surface 12 that promotes the formation of a polarized monolayer. Many other coatings that function to provide a water and ion permeable attachment layer, which promotes the formation of a polarized monolayer will be apparent to one of skill in the art in light of the disclosure herein and are equivalents to the structures discussed above.

While investigating an approach to engineer intestinal tissue, Mooney et al. reported the construction of a tubular and biodegradable support which promoted vascularization following implantation. (Mooney et al., *Cell Transplant*, 3:203–210 (1994), herein incorporated by reference). A similar design support 10 is contemplated for the construction of embodiments of the artificial salivary gland 20 that promote the polarization, growth, and organizational behavior of allogeneic graft cells 14, which are capable of unidirectional salt and water movement in response to autonomic neurotransmitter stimulation. (See Baum et al., *Ann. NY Acad. Sci.*, 694:17–23 (1993)).

Although many types of supports 10 can be used with embodiments of the invention preferably, but not by way of limitation, the support 10 is porous, biodegradable in the body of a subject, and ion and water-permeable. Biodegradable supports 10 are favored because the artificial fluid secreting device 20 can induce immunotolerance to the donor cells 14 (especially if they are allogeneic cells) as the support disintegrates and thereby establish a chimeric population of cells 14 in the subject. Advantageously, several biodegradable supports 10 used with embodiments of the invention are also substantially water and ion permeable so as to enable the artificial salivary gland 20 to act as a pump from surrounding tissues. Preferred biodegradable supports 10 are poly-L-lactic acid [PLLA] and polyglycolic acid [PGA] but several others will be apparent to those of skill in the art. Example 1 describes a method for identifying and constructing suitable supports 10. The next section describes embodiments of the artificial salivary gland 20 that have been designed to hinder migration after implantation.

Embodiments of the artificial salivary gland can prevent migration after implantation Embodiments of the artificial fluid secreting device 20 can also have enhancements that promote stability and resistance to movement. In general, an attachment surface 22 can be included on the artificial fluid secreting device 20 or can be included on an attachment that is directly or indirectly connected to the artificial fluid secreting device 20 so that the device 20 can be positioned and retained in the desired position. The attachment surface 22 can be additionally, or alternatively, provided with any of a variety of tissue retention structures such as hooks, barbs, tacks, clips, sutures, staples, tissue adhesives, attachment strips, attachment connectors, or other attachment means, which will be understood by those of skill in the art in view of the disclosure herein.

One embodiment, for example, has a novel attachment surface 22 appropriately spaced about the device 20 so as to facilitate tissue ingrowth. Advantageously, this embodiment of the artificial salivary gland 20 stabilizes and maintains the device 20 in a predetermined location within or about salivary gland orifices or ducts. The design and spacing of the attachment surfaces 22 are selected according to the ability to permit sufficient cellular ingrowth and to provide a long-term fixation against both proximal and distal axial migration of the device 20 but enable removal with little trauma to the subject. The ease of removal of the artificial fluid secreting device 20 is desirable for non-biodegradable implants, for example, so that the changing anatomy of a subject can be accommodated.

In one embodiment, the attachment surface 22 can be positioned proximally of the distal end 18 and comprise a tissue ingrowth surface thereon. Alternatively, the tissue ingrowth surface 22 can extend throughout the length of the artificial fluid secreting device 20. Further, the attachment surface 22 can be provided concentrically around the artificial fluid secreting device 20. By one approach, the attachment surface 22 comprises a porous surface that promotes cellular ingrowth. The porosity of the cellular ingrowth regions 22 can range from about 0.2 $\mu$m to about 100.0 $\mu$m or greater. Desirably, the porosity of the cellular ingrowth regions 22 range from 0.2 $\mu$m to 50 $\mu$m and, preferably, the porosity of the cellular ingrowth regions 22 range from 0.21 $\mu$m to 20 $\mu$m.

Suitable attachment surface 22 materials include polytetrafluoroethylene (PTFE), polyethylene terephthalate, polyester, polyurethane, silicone, dacron, polypropylene knit, and other materials, which will be apparent to those of skill in the art in view of the present disclosure. In another embodiment, the region of cellular ingrowth 22 comprises PTFE having a 0.22 $\mu$m pore size. This porosity permits shallow ingrowth into the artificial fluid secreting device 20 and prevents axial migration of the device 20 along tissue planes yet allows for easy explant.

In any of the foregoing embodiments, the artificial fluid secreting device 20 can comprise either an integrally formed support 10, or a support 10 fabricated from two or more components or surface treatments. The attachment surface 22 on the support 10, for example, is preferably provided with a microporous structure to facilitate tissue ingrowth, as detailed above. The support 10 of the artificial fluid secreting device 20 can be manufactured as a unitary or multi-component structure in a variety of ways as will be appreciated by those of skill in the art in view of the disclosure herein.

Alternatively, the support 10 of the artificial fluid secreting device 20 can comprise at least two components connected together and can be made, for example, by attaching an outer sleeve of porous material such as expanded polytetraflouroethylene (PTFE) or other tissue ingrowth material 22 to the device 20 by bonding the two materials together. If expanded PTFE is used, a PTFE surface etching step prior to bonding with a silicone based glue can be performed, or alternatively, a process of gluing by simultaneously compressing and heating the stack-up of foam, glue and PTFE can be employed. The attachment layer 22 can be secured to the artificial fluid secreting device 20 in any of a variety of manners, such as by solvent bonding, thermal bonding, adhesives, and others as will be apparent to those of skill in the art in view of the disclosure. The section below describes embodiments that have a monolayer of allogenic or autologous cells, which express and secrete a product from a transgene (e.g., protein).

Embodiments of the Artificial Salivary Gland Can Have a Monolayer of Allogeneic Cells That Express and Secrete a Product from a Transgene Some embodiments of the artificial fluid secreting prosthetics 20 have a monolayer of cells 14 that are engineered to express and secrete molecules including, but not limited to, water, ions, enzymes, glycoproteins, and therapeutic and/or prophylactic agents. See Examples 2 and 3. Although a number of secretory cells can be engineered, using conventional techniques in molecular biology, to accomplish these tasks, allogeneic or autologous cell lines are preferred. Desirably, allogeneic cell lines are used for manufacturing convenience. Conventional immunosuppressive agents, such as cyclophosphamide, cyclosporin, tacrolimus (FK506), azathioprine, prednisone, methylprednisolone, prostaglandin, and steroids, can also be administered, as is known in the art, in conjunction with the implant to quash the tissue rejection response and promote immunotolerance.

Several types of secretory epithelial cell lines can be used with embodiments of the invention. Preferably, epithelial cells from the subject are removed by conventional techniques and are cultured in vitro so as to produce a population of autologous cells in culture. The cultured autologous cells can then be manipulated using techniques in molecular biology (e.g., transfection with an expression construct) to express desired proteins such as water or ion channel proteins. Subsequently, the autologous cells 14 expressing the desired protein are used to seed a support 10 and thereby create an artificial salivary gland that is specific for the subject from whom the epithelial cells were removed.

In many cases, however, a stable in vitro culture of salivary gland epithelial cells from a subject will not be obtainable. For this situation, the construction of an artificial salivary gland 20 comprising cells 14 cultured from a human submandibular gland cell line, termed "HSG", is appropriate. (Shirasuna et al., Cancer, 3:203–210 (1981)). The phenotype of these cells 14 is desirably responsive to different extracellular matrix components 12. Further, HSG cells 14 are useful targets for gene transfer methods and can utilize established salivary gland cell-specific promoter elements.

(Mastrangeli et al., Am. J. Physiol., 266:G1146–G1155 (1994)). Other cells 14 can be used in accordance with aspects of the invention, however, and those of skill in the art could readily adapt the teachings herein to further this end.

Cells 14 used to construct the artificial salivary gland 20 are preferably transfected with genes that encode the desired protein responsible for water and ion transport or protein, glycoprotein, enzyme, and therapeutic and/or prophylactic agent secretion prior to seeding on the support. In this manner, the cells 14 can be sufficiently screened for the presence of the gene(s) and a robust population of cells 14 expressing the desired gene(s) can be obtained. By example only and not by way of limitation, one preferred embodiment comprises HSG cells 14 transfected with an expression construct having a gene of the aquaporin family (e.g., aquaporin-1 (AQP1) (Delporte et al., Proc. Natl. Acad. Sci. USA, 94:3268–3273 (1997)) or aquaporin-5 (AQP5). AQP1 is the archetypal mammalian water channel protein (Preston and Agre, Proc. Natl. Acad. Sci USA, 88:11110–11114 (1991)) and the use of other water channel proteins are contemplated with embodiments of the present invention. (See U.S. Pat. Nos. 5,741,671 and 5,858,702 to Agre, which disclose the isolation, cloning, and expression of AQP1 and AQP5). Additionally, some embodiments have recombinant constructs comprising a "suicide gene", such as HSV-thymidine kinase, which can be used to destroy the cell if growth control becomes compromised in a subject. In the example that follows, a method for identifying and constructing suitable supports 10 is provided.

Vectors for use with embodiments of the invention can be varied according to the cell type used to express the transgene and the mode of transfection or gene transfer. Adenoviral vectors are used with some embodiments but, preferably, transgenes are transferred to the cells that compose embodiments of the invention using an adenoassociated virus or a hybrid adenoretrovirus. Cationic liposomes are also used to transfer trangenes to salivary cells in some embodiments. Example 1 describes a method for identifying and constructing suitable supports for attaching the engineered cells of the invention.

EXAMPLE 1

In an initial study, the growth and organizational behavior of salivary epithelial cells on a support 10 was analyzed. The support 10 was constructed from a quartered denuded rat trachea and was coated with a matrix molecule such as Matrigel, fibronectin, laminin, collagen I, collagen IV, and gelatin. After preparation of the coated support 10, a salivary epithelial cell suspension was provided to the coated support 10 and cellular growth and morphology was observed by microscopy. Microscopic analysis revealed that the matrix molecules provided a surface 12 that promoted the formation of a polarized monolayer of cells 14 on the support 10.

In a second study, the growth and organizational behavior of allogeneic graft cells on two biodegradable polymer supports 10—poly-L-lactic acid [PLLA] and polyglycolic acid [PGA] was analyzed. A human submandibular gland cell line, termed "HSG" (Shirasuna et al., Cancer, 3:203–210 (1981)) was used as the prototype graft cell 14 because their phenotype is highly responsive to different extracellular matrix components 12 and HSG cells 14 exhibit intact $Ca^{2+}$signaling systems, such as required to regulate salivary fluid secretion. Additionally, HSG cells 14 have ion channels that can be utilized to generate the necessary osmotic gradients. Since native salivary eipthelia exist essentially as a monolayer lining a lumen, an ideal substrate 12 induces HSG cells 14 to form a polarized monolayer, which affords a complete coverage of the support 10.

In this study, supports 10 with and without a protein-coating 12 were seeded with HSG cells 14 and, once confluence was achieved, the adherent cells 14 were analyzed with laser scanning confocal microscopy. The protein-coatings 12 examined were fibronectin (FN), laminin (LN), collagen IV, Vitrogen (a commercial collagen I preparation), and gelatin. Prior to seeding with HSG cells 14, each ECM-coating 12 was applied at 20 μg/ml to separate supports 10 by conventional methods.

In controls that lacked a protein-coating 12, the HSG cells 14 did not attach to either PLLA or PGA. In contrast, FN-coated PLAA promoted the formation of a stable HSG cell monolayer. By laser scanning confocal microscopy the adherent HSG cells 14 on the FN-coated supports 10 were observed to have several required junctional complex and matrix interactive proteins including β-catenin and paxillin. HSG cells 14 also adhered to collagens I and IV, and LN coated supports 10 in a monolayer, though not as securely as the FN-coated support 10. The study above demonstrated that a desirable salivary cellular organization could be obtained on a biodegradable support 10, such as PLLA or PGA. By using the approach detailed above, several different types of supports 10 can be rapidly analyzed and prepared. The example below describes various approaches to create cells 14 that express a desired gene.

EXAMPLE 2

In mammalian host cells, a number of viral-based expression systems can be utilized. In cases where an adenovirus is used as an expression vector, the nucleotide sequence of interest (e.g., AQP1) can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the AQP1 gene product in infected hosts. (See eg., Logan & Shenk, *Proc. Natl. Acad. Sci. USA* 8 1:3655–3659 (1984)).

Specific initiation signals can also be required for efficient translation of inserted AQP1 nucleotide sequences. These signals include the ATG initiation codon and adjacent sequences. In cases where an entire AQP1 gene or cDNA, including its own initiation codon and adjacent sequences, is inserted into the appropriate expression vector, no additional translational control signals can be needed. However, in cases where only a portion of the AQP1 coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See e.g., Bittner et al., *Methods in Enzymol*, 153:516–544 (1987)).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used.

For long-term, high-yield production of recombinant proteins, stable expression is preferred. For example, cell lines that stably express the AQP1 sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines that express the AQP1 gene product.

A number of selection systems can be used, including but not limited to the herpes simplex virus thymidine kinase (Wigler, et al., *Cell* 11:223 (1977), hypoxanthine-guanine phosphoribosyltransferase (Szybalska & Szybalski, *Proc. Natl. Acad. Sci. USA* 48:2026 (1962), and adenine phosphoribosyltransferase (Lowy, et al., *Cell* 22:817 (1980) genes can be employed in tk.sup.-, hgprt.sup.- or aprt.sup.- cells, respectively. Also, antimetabolite resistance can be used as the basis of selection for the following genes: dhfr, which confers resistance to methotrexate (Wigler, et al., *Proc. Natl. Acad. Sci. USA* 77:3567 (1980), O'Hare, et al., *Proc. Natl. Aced. Sci. USA* 78:1527 (1981); gpt, which confers resistance to mycophenolic acid (Mulligan & Berg, *Proc. Natl. Acad. Sci. USA* 78:2072 (1981); neo, which confers resistance to the aminoglycoside G-418 (Colberre-Garapin, et al., *J. Mol. Biol.* 150:1 (1981); and hygro, which confers resistance to hygromycin (Santerre, et al., *Gene* 30:147 (1984)).

By one approach, to express the proteins encoded by the AQP1 gene, nucleic acids containing the coding sequence for AQP1 are obtained and cloned into a suitable expression vector such that the coding region is operably linked to a heterologous promoter. The expression vector is desirably a mammalian expression vector and preferably a human expression vector. Many commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). U.S. Pat. Nos. 5,741,671 and 5,858,702 to Agre also disclose the preparation of expression constructs for AQP1 and AQP5.

If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767. Further, a secretory leader sequence can be incorporated so as to promote secretion of the protein. This aspect is particularly useful for the design of drug delivery systems that administer a therapeutic agent, which is normally not a secreted protein. Many vectors or recombinant constructs having genes that encode therapeutic agents for which blood stream delivery is desired can be used with embodiments of the invention. As demonstrated above, the delivery of molecules such as hGH to the blood stream by transfected cells 14 of the salivary gland is possible and the blood stream delivery of hGH and other therapeutic agents by cells 14 of an artificial salivary gland transfected with an expression construct encoding hGH or another therapeutic agent is expected.

To make the AQP1 construct, first, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the desired cDNA lacks a poly A signal, this sequence can be added to the construct by, for example, splicing out the Poly A signal from pSG5 (Stratagene) using BgII and SaII restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for Pst I incorporated into the 5 primer and BglII at the 5 end of the corresponding cDNA 3 primer, taking care to ensure that the nucleic acid is positioned in frame with the poly A signal. The purified fragment obtained from the resulting PCR reaction is digested with PstI, blunt ended with an exonuclease, digested with BgI II, purified and ligated to pXT1, now containing a poly A signal and digested with BglII. The ligated product is transfected into a suitable cell line, e.g., HSG cells 14, using Lipofectin (Life Technologies, Inc., Grand Island, N.Y.) under conditions outlined in the product specification. Positive transfectants are selected after growing the transfected cells in 600 μg/ml G418 (Sigma, St. Louis, Mo.). Preferably, the culture medium is screened for the expressed protein by conventional assays (Western blot, sandwich assays or ELISA) so as to verify protein expression and the secretory ability of the cells 14 prior to seeding the support 10. If the desired protein is a transport protein such as AQP1 or AQP5 rather than a secreted protein then alternative assays are employed to verify the functionality of the transporter as encoded by the expression construct. U.S. Pat. Nos. 5,741,671 and 5,858,702 to Agre, herein incorporated by reference, disclose several approaches to analyze the functionality of AQP1 and AQP5 in cells and xenopus oocytes. Several other assays to monitor the functionality of ion transport proteins are provided in the following example.

EXAMPLE 3

One approach developed for labeling functional ion channels is based on the physical flow of conducting ions through the channel of interest. For one pico amp of ionic current, roughly $10^6$ ions is pass can through an ion channel. By utilizing the property of monovalent thallium (T($I^+$)) ions to crystallize at very low concentration with halide ions, such as $Br^-$, functional ion channels can be labeled. Operationally, once thallium ions are applied to one side of the membrane, they will pass through the channel pores, create a local increase in thallium concentration, and eventually crystallize with Br ions that are present on the other side of the membrane. The crystals grow to a visible size and thus mark the location of ion channels on the membrane (See, e.g., Lopatin et al., *Biophysical Journal* 74:2159–2170 (1998), herein incorporated by reference).

In one method, a first group of xenopus oocytes are injected with roughly 5 ng of cRNA encoding the desired ion channel into the animal (dark) hemisphere (pole) and a measurement of oocyte current and membrane potential are recorded so as to provide a baseline value. As a control, the current and membrane potential of a second group xenopus oocytes that have been injected with roughly 5 ng of a non-protein coding cRNA is measured. The two groups of ooctyes are then injected with roughly 50 nl of 30 mM KBr, so as to bring the intracellular concentration of KBr to roughly 3 mM, and voltage-clamped with a 2-microelectrode voltage clamp in a thallium-containing solution. 40×410 ms linear voltage ramps from −80 mV to +50 mV are then applied at a frequency of 0.75 Hz to drive the inward flow of thallium ions and the ionic currents are recorded. The two groups of oocytes are then photographed. Multiple white crystals will be visible by light microscope on the animal hemisphere if the protein expressing oocytes allow for ion transport. By comparing the relative abilities of the two groups of oocytes to crystalize thalium, one of skill in the art can easily determine the extent to which the desired protein functions as an ion transporter.

In an alternative method, liposomes having the desired protein are loaded with bromine ions (Br). Subsequently, the liposomes having the desired protein are contacted with thallium ions and electrical current is applied. The local increase in thallium concentration inside the liposome is detected by microscopic observation of crystals which form at the location of the ion channels.

To directly measure ion transport, an agarose-hemi-clamp technique based on the capacity of agarose to electrically conduct ions as well as free solution while obviating the bulk flow of ions is used. By this approach, oocytes expressing the desired and oocytes expressing a control protein are voltage-clamped in a TICI bath solution, and 2 microelectrodes are used to record ion currents. Subsequently, the clamp circuit is switched off, the electrodes are removed, and the cell is completely embedded in 1% agar in the TICI solution. After the agar is set and cooled to room temperature, the piece of gel containing the cell is cut out and the cell is voltage-clamped again. By comparing the relative abilities of the oocytes expressing the desired protein and the oocytes expressing the control protein to conduct electricity, one of skill in the art can easily determine the extent to which the desired protein functions as an ion transporter.

By an alternative approach, an impedance analysis of ion transport through a support having the desired protein immobilized thereon is determined. (Steinem et al., *Bioelectro Chemistry and Bioenergetics*, 42:213–220, (1997), herein incorporated by reference). In this embodiment, a support is constructed by reconstituting the desired protein into large unilamellar vesicles (LUV) of dimethyidioctadecylammoniumbromide (DODAB), which are then fused onto a negatively charged monolayer of 3-mercaptopropionic acid (MPA). An initial determination of impedance in the presence of different monovalent cations at varying concentrations is then made for the two types of multimeric supports. A.C. impedance spectroscopy, as an integral electrochemical method, is used because it offers the possibility to determine the electric parameters of thin films such as biomembranes without redoxactive marker ions. Thus, ions that permeate the membrane exhibit a resistance parallel to the membrane capacitance and in series to the capacitance of the substrate.

A.C. impedance analysis is performed using an SI 1260 impedance gain/phase analyzer from Solartron Instruments (Great Britain) controlled by a personal computer, however, those of skill in the art would be able to use other A.C. impedance analyzers. To prepare the support, gold electrodes are exposed for about 10 minutes to a 10 mM solution of the MPA so as to form a highly oriented self-assembled monolayer. Afterwards, the electrodes are rinsed extensively with a Tris buffer solution pH 8.6 to remove any remaining physisorbed molecules. To control the surface coverage and, therefore, the quality of the film, each step is monitored by impedance spectroscopy. A capacitance of about 9 mM F/cm$^2$ is a reference value for a successfully deposited monolayer.

Large unilamellar vesicles (LUV) of DODAB (1.5 mg/ml) with 1 mol % of the desired protein are prepared by a method of extrusion in the same buffer solution, as known by those of skilled in the art. (Steinem et al., Biochim. Biophys. Acta 1279:169–180 (1996)). The LUV vesicles are added to the prepared MPA monolayer in the electrochemical cell. A bilayer is formed at room temperature without stirring the solution. After one hour, the process is finished and the vesicle suspension is replaced by pure buffer.

The formation of the solid supported bilayer is then observed by impedance spectroscopy and measurements are taken in the absence of ions. Subsequently, impedance measurements are taken in the presence of different concentrations of LiCl, NaCl, KCl, and CsCl. After addition of different concentrations of one kind of ion to the DODAB bilayer, the solution is replaced by pure buffer and an impedance spectrum is recorded in order to ensure that the solid supported bilayer was not disrupted. The extent to which the desired protein has the ability to transport the particular ion will be ascertainable given that the impedance of the electrochemical system decreases significantly as the concentration of the ion increases.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. An article of manufacture comprising:
   a) a water and salt permeable, porous biodegradable blind end tube having an interior surface,
   b) matrix components coating said interior surface capable of promoting the formation of a polarized monolayer of salivary gland epithelial cells, and
   c) a polarized monolayer of salivary gland epithelial cells, said salivary gland epithelial cells disposed on said interior surface and having a phenotype in which said salivary gland epithelial cells express or are transduced to express a water channel protein and ion transport protein so that water and salt is secreted unidirectionally.

* * * * *